US00PP13619P2

(12) United States Plant Patent
Trees

(10) Patent No.: US PP13,619 P2
(45) Date of Patent: Mar. 4, 2003

(54) ANTIRRHINUM PLANT NAMED 'BALUMDELO'

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/109,508

(22) Filed: Mar. 27, 2002

(51) Int. Cl.[7] ..... A01H 5/00
(52) U.S. Cl. ..... Plt./322
(58) Field of Search ..... Plt./322

*Primary Examiner*—Kent Bell
(74) *Attorney, Agent, or Firm*—Wood, Phillips, Katz, Clark & Mortimer

(57) ABSTRACT

A new and distinct Antirrhinum plant named 'Balumdelo', characterized by its dark yellow flowers, mounded and trailing habit, and dark green leaves.

1 Drawing Sheet

LATIN NAME OF THE GENUS AND SPECIES OF PLANT CLAIMED

*Anthirrhinum majus.*

VARIETY DENOMINATION

'Balumdelo'.

BACKGROUND OF THE INVENTION

The present invention comprises a new and distinct Antirrhinum plant, botanically known as *Antirrhinum majus,* and hereinafter referred to by the cultivar name 'Balumdelo'. The new cultivar was developed by the inventor through a controlled breeding program during 1998 at Arroyo Grande, Calif. The objective of the breeding program was the development of Antirrhinum cultivars with mounded trailing habit, continuous flowering, excellent basal branching and small, dark green leaves.

The female (seed) parent of 'Balumdelo' was the proprietary Antirrhinum breeding selection designated 445-1, which exhibits a semi-trailing habit, lavender and yellow bicolor flowers and medium green foliage. The male (pollen) parent of 'Balumdelo' was the proprietary Antirrhinum breeding selection designated 488-3, which exhibits a vigorous trailing habit, lavender flowers and dark green foliage. The new cultivar was discovered as a single flowering plant from within the progeny of the above stated cross in December 1999 and was initially designated 1606-1.

Asexual reproduction of the new cultivar has been carried out at Arroyo Grande, Calif. and West Chicago, Ill. by terminal tip cuttings and has demonstrated that the characteristics of the new cultivar as herein described are firmly fixed and retained through successive generations of such asexual propagation.

SUMMARY OF THE INVENTION

It was found that the cultivar of the present invention:

(a) Exhibits dark yellow flowers;
(b) Forms dark green foliage;
(c) Exhibits a good basal branching character; and
(d) Exhibits a trailing growth habit.

The new cultivar of the present invention can be compared to 'Balumyell' (co-pending U.S. Plant patent application Ser. No. 09/808,089). In side-by-side comparisons, 'Balumdelo' is more compact and differs in flower color from 'Balumyell'. When compared to its sibling 'Balumbreo' (co-pending U.S. Plant patent application Ser. No. 10/109,509), 'Balumdelo' is found to be more compact and differs in flower color.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill.

DETAILED BOTANICAL DESCRIPTION

The cultivar 'Balumdelo' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 18, 2001. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown utilizing a soilless growth medium with temperatures of approximately 65° to 75° F. (18° to 24° C.) during the day and approximately 50° to 55° F. (10° to 14° C.) during the night and light levels of 5,000 to 6,000 footcandles being maintained. Plants used for the following descriptions and measurements were grown in 10 cm pots for 12 weeks from rooted cuttings.

Classification:
*Botanical.*—*Antirrhinum majus* cultivar 'Balumdelo'.
Parentage:
*Female parent.*—Proprietary Antirrhinum selection designated 445-1.

*Male parent.*—Proprietary Antirrhinum selection designated 488-3.

Propagation:

*Type cutting.*—Terminal tip.

*Time to initiate roots.*—Approximately 7 to 10 days.

*Time to develop roots.*—Approximately 14 to 21 days.

*Root description.*—Fibrous, branching.

Plant description:

*Habit of growth.*—Vigorous with good basal branching. Pinching improves basal branching. A mature plant, 12 weeks after the planting of a rooted cutting, measures approximately 10.5 cm in height and approximately 29.5 cm in diameter with an average of 5.3 branches.

*Form.*—Mounded and trailing.

*Stem.*—Approximately 11.8 cm in length, 2 mm in diameter, densely pubescent and between 146A and 147A. Internode length is approximately 1.4 cm.

*Foliage.*—Leaves are non-fragrant, single, opposite and at an acute angle to the stem. Leaves are ovate with entire margin, acute apex and attenuate base. Upper and lower surfaces are puberulent. Leaf length is approximately 4 cm and width is approximately 2.5 cm. Upper surface of mature foliage is 147A, lower surface of mature foliage is 147B. Both upper and lower surfaces have pinnate venation closest to 144C. Petiole length is approximately 7 mm, diameter is approximately 2 mm, surface is puberulent and color is between 147A and 147B.

Flowering description:

*Flowering habit.*—Freely flowering.

*Natural flowering season.*—Year round in greenhouse environment and spring through autumn in outdoor garden.

*Lastingness of the bloom (on the plant).*—Approximately ten days.

*Flower arrangement.*—Terminal racemes.

*Peduncle.*—Strong, glandular, at an acute angle to the stem, approximately 7 mm in length and 1 mm in diameter. Peduncle color is 137C.

*Flower bud.*—Obovate, approximately 2.3 cm in length and 1.7 cm in diameter. Bud color is 145A. Texture is villous.

*Flower description.*—Flowers are bilabiate. The upper lip has two obovate lobes with rounded tips, entire margins, and attenuate bases. The lower lip has three obovate lobes with rounded tips, entire margins, and attenuate bases. Flower length is approximately 3.3 cm and width is approximately 2.3 cm. Color of fully open flowers: Upper surface of upper lip is 1A with veins of 59B radiating from base. The upper surface of the lower lip is darker and more orange than 1A. The undersurface of the upper and lower lips is 162C with venation of 183D. The upper surface of the palate is 155D. The undersurface of the palate is 1D. Inside throat is 155D with hairs of 155D. Outside throat is 155D with the lower ½ of 1C.

*Sepals.*—Five, approximately 8 mm in length and 4 mm in width with acute apex and entire margin. Both upper and lower surfaces are pubescent and 137B.

*Reproductive organs.*—Androecium: There are 4 stamens-2 are approximately 2 cm in length and 2 are approximately 1.3 cm in length. Anthers are 2 mm in length and 16D in color. Pollen is abundant and color is 16C. Gynoecium: One pistil, 1.5 cm in length. Stigma is 3 mm in length and color is 154D. Style length is 8 mm and color is 7C just below the stigma and 154D just above the ovary. Ovary length is 4 mm, texture is densely pubescent and color is 143B.

Seed production: Seed production has not been observed.

Disease resistance: Resistance to pathogens has not been observed.

I claim:

1. A new and distinct cultivar of Antirrhinum plant named 'Balumdelo' substantially as herein shown and described, which:

(a) Exhibits dark yellow flowers;
(b) Dark green foliage;
(c) A good basal branching character; and
(d) A mounded and trailing growth habit.

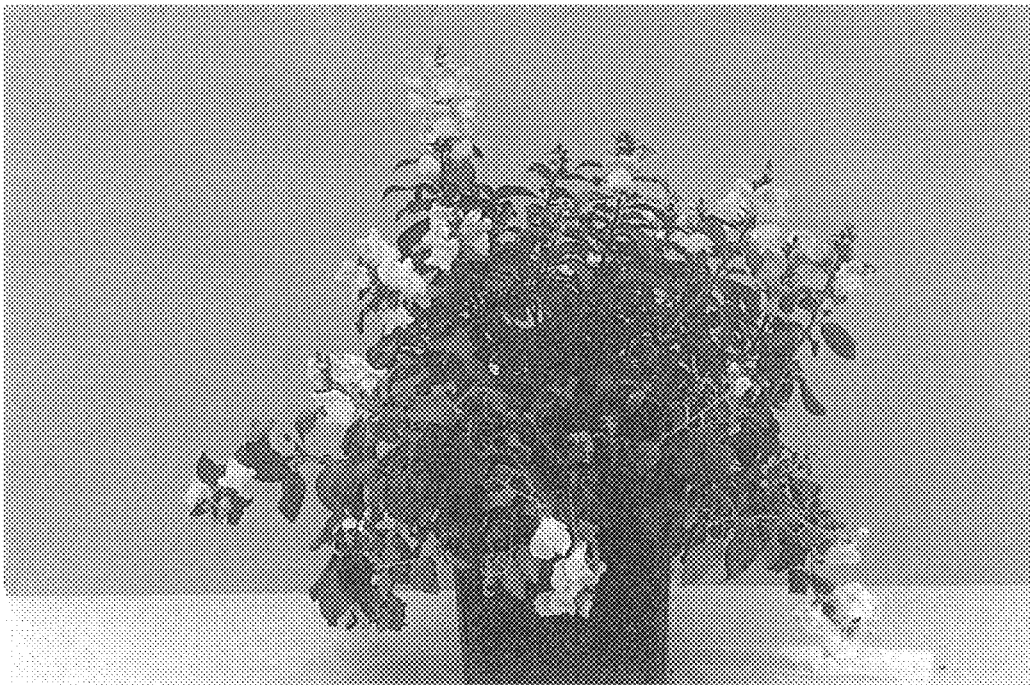

* * * * *